United States Patent [19]
Krstenansky

[11] Patent Number: 5,834,433
[45] Date of Patent: Nov. 10, 1998

[54] COMPOUNDS AND PHARMACEUTICAL USES OF PEPTIDES OF BOMBESIN AND GRP

[75] Inventor: John L. Krstenansky, Palo Alto, Calif.

[73] Assignee: Merrell Pharmaceuticals Inc., Cincinnati, Ohio

[21] Appl. No.: 960,130

[22] Filed: Feb. 23, 1996

Related U.S. Application Data

[63] Continuation of Ser. No. 447,528, May 23, 1995, abandoned, which is a continuation of Ser. No. 278,692, Jul. 21, 1994, abandoned, which is a continuation of Ser. No. 735,402, Jul. 24, 1991, abandoned, which is a continuation-in-part of Ser. No. 558,031, Jul. 26, 1990, abandoned.

[51] Int. Cl.$^6$ .......................... A61K 38/00; A61K 38/02; C07K 5/00; C07K 7/00
[52] U.S. Cl. ................................ 514/16; 514/17; 530/329
[58] Field of Search .................................. 514/14, 15, 16, 514/17; 530/326, 327, 329

[56] References Cited

U.S. PATENT DOCUMENTS

| | | |
|---|---|---|
| 4,297,346 | 10/1981 | Rips et al. . |
| 4,331,661 | 5/1982 | Marki et al. ............................ 424/177 |
| 4,421,744 | 12/1983 | Gormley et al. . |
| 4,613,586 | 9/1986 | Barchas et al. . |
| 4,631,270 | 12/1986 | Yankeelovi et al. . |
| 4,871,717 | 10/1989 | Coy et al. . |
| 5,019,647 | 5/1991 | Rieman et al. . |
| 5,028,692 | 7/1991 | Oliff et al. . |
| 5,047,502 | 9/1991 | Oliff et al. ............................. 530/329 |

FOREIGN PATENT DOCUMENTS

| | | |
|---|---|---|
| 2710288 | 4/1989 | Australia . |
| 2414288 | 5/1989 | Australia . |
| 3588189 | 12/1989 | Australia . |
| 2414288 | 6/1990 | Australia . |
| 2710288 | 4/1992 | Australia . |
| 0309297 | 3/1989 | European Pat. Off. . |
| 0313158 | 4/1989 | European Pat. Off. .......... C07K 7/06 |
| 0315367 | 5/1989 | European Pat. Off. .......... C07K 7/00 |
| 0339193 | 11/1989 | European Pat. Off. . |
| 0345990 | 12/1989 | European Pat. Off. . |
| 0371543 | 6/1990 | European Pat. Off. . |
| 0434979 | 7/1991 | European Pat. Off. . |
| 0468497 | 1/1992 | European Pat. Off. . |
| 8909232 | 10/1989 | WIPO . |
| 9001037 | 2/1990 | WIPO . |
| 9003980 | 4/1990 | WIPO . |
| 9106563 | 5/1991 | WIPO . |
| 9117181 | 11/1991 | WIPO . |
| 9209626 | 6/1992 | WIPO . |

OTHER PUBLICATIONS

COy, David, H., et al., J. Biol. Chem., 263(11), 5056–5060 (1988).
Cowan, et al., Life Sciences, 37:135–145 (1985).
Corps, et al., Biochem. J. 231:781–784 (1985).
Dickinson, et al., Biochemical and Biophysical Research Communications, 157(3):1154–1158 (1988).
Erspamer, et al., Regulatory Peptides 21:1–11 (1988).
Erspamer, et al., Peptides 5:765–768 (1984).
Miller, Am. J. Respir. Cell Mol. Biol. 3:189–190 (1990).
Miller, Am. Rev. Respir. Dis. 140:283–284 (1989).
Mukia, et al., Am. J. Physiol 257:E235–E240 (1989).
Rossowski, et al., Scand. J. Gastroenterol., 24, 121–128 (1989).
Schrenck, et al., Am. J. Physiol. 256 (Gastrointest. Liver Physiol. 19):G747–G758 (1989).
Pappas, et al., Peptides 6:1001–1003 (1985).
Sunday, et al., Am. J. Respir. Cell Mol. Biol. 3:199–205 (1990).
Trepel, et al., Biochemical and Biophysical Research Communications 156(3):1383–1389 (1988).
Van Tol, et al., Neuropeptides 18:15–21 (1991).
Tache, et al., Life Sciences 37:115–123 (1985).
Zachary, et al., Biochemical and Biophysical Research Communications, 137(1):135–141 (1986).
Yachnis, et al., Life Sciences, 35:1963–1969 (1984).
Heinz–Erian, et al., Am. J. Physiol. 252:G439–G442 (1987).
Anti, et al., Biological Abstracts, 73(2):1267 abstract #12334 (1981).
Basso, et al., Biological Abstracts, 64(1):abstract #4199 (1977).
Mahmoud, S., et al., Life Sciences, 44(5), 367–373 (1989).
Bologna, Mauro, et al., Cancer, 63, 1714–1720 (1989).
Jensen, R.T., et al., Nature, 309, 61–63 (1984).
Coy, David H., et al., J. Biol. Chem., 264(25), 14691–14697 (1989).
Cowan, Alan, TIPS, 101, 1–3 (1988).
Heimbrook, David C., et al., J.Biol. Chem.264(19), 11258–11262 (1989).
Heimbrook, David D., UCLA Symp., Mol. Cel. Biol., 86, 295–307 (1989).
Saeed, Z.A., Peptides, 10, 597–603 (1989).
Woll, Pennela, J. et al., Proc. Natl. Acad. Sci. USA, 85, 1859–1863 (1988).
Zhang, Li, et al., Biochimica et Biophysica Acta 972, 37–44 (1988).
Woll, Pennela, J. et al., Growth Factors, 1, 75–83 (1988).
Bepler, Gerold, et al., Peptides, 9, 1367–1372 (1989).
Merali, Zul, et al., Synapse, 2, 282–287 (1988).

(List continued on next page.)

*Primary Examiner*—Avis M. Davenport
*Attorney, Agent, or Firm*—T. Helen Payne

[57] ABSTRACT

A method for controlling the growth of tumor tissues, especially small cell lung. Treatment comprises administering to a patient in need thereof, an effective amount of a bombesin/GRP type inhibitor.

Antagonists of bombesin/GRP which are derivatives of naturally occurring bombesin/GRP possessing a thiomethylene or methylene sulfoxide bond connecting the two amino acids on the carboxy terminal end is modified are described. The antagonism is confirmed using conventional competitive binding and biochemical assays as well as conventional physiological tests and the use of these derivatives in a variety of conditions in which bombesin/GRP is implicated is also described.

8 Claims, No Drawings

OTHER PUBLICATIONS

Dutta, Anand S., et al., J. Med. Chem. 29, 1171–78 (1986).

Marki, et al., Peptides, 2(2) 169–177 (1981).

Lebacq–Verheyden, A.M., et al., Bombesin and Gastrin Releasing Peptide: Neuropeptides, Secretogogues, and Growth Factors, Chapter 21, In Peptide Growth Factors and Their Receptors II, editors Sporn, M., and Roberts, A.B., Springer–Verlag, NY, (1990).

Edwards, J.V., et al, 1990 Gordon Conference on the Chemistry and Biology of Peptides, Feb. 5–9, 1990 Ventura, CA.

Antony, V.B., et al., Clin. Res. 37, 145A (1989).

Woll, P.J., et al., BBRC, 155(1), 359–365 (Aug. 1988).

Spatola, A.F., et al., Chem. Abs. 111, abst. No. 90576e, p. 96 (1989).

Smith, C.W., et al., Chem Abs. 109(3), abst. No. 23372f, p. 662 (1988).

Edwards, J.V., et al., BBRC 136(2), 730–6 (1986).

Edwards, J.V., et al., Int. J. Peptide Protein Res. 28, 603–612 (1986).

Edwards, J.V., et al., 1992 Gordon Conference—Peptides, Chemistry and Biology, Ventura, California, Feb. 9–14, 1992.

Kinzie, et al., American Federation for Clinical Research, Carmel, CA, Feb. 5–8, 1992.

Edwards, et al., Peptide Analogs of Bombesin and Litorin as Receptor Antagonists and Agonists. To be Published.

Krstenanasky, et al., 22nd National Medicinal Chemistry Symposium, 1990.

Fanger, et al., J. Cell Biochem. 15B:123, 1991.

Edwards, et al., Int'l. Journal of Peptide & Protein Research, 43, 374–383 (1994).

Edwards, et al., Proceedings of the 13th American Peptide Symposium, Robert S. Hughes and John A. Smith, pp. 500–507, ESCOM–Leiden (1994).

Bepler et al., Peptides, vol. 9, pp. 1367–1372, 1989.

Miller, Am J. Respir. Cell Mol. Biol., vol. 3, pp. 189–190, 1990.

Heimbrook et al., J. Biol Chem., vol. 264, No. 19 pp. 11258–11262, 1989.

Heimbrook et al., UCLA Symp Mol. Cell Biol., vol. 86, pp. 295–307, 1989.

COMPOUNDS AND PHARMACEUTICAL USES OF PEPTIDES OF BOMBESIN AND GRP

CROSS-REFERENCE TO RELATED APPLICATIONS

This is a continuation, of application Ser. No. 08/447,528, filed May. 23, 1995, which is a continuation of application Ser. No. 08/278,692, filed Jul. 21, 1994 ; now abandoned; which is a continuation of application Ser. No. 07/735,402, filed Jul. 24, 1991, now abandoned; which is a continuation-in-part of application Ser. No. 07/558,031, filed Jul. 26,1990, now abandoned, which is herein incorporated by reference.

FIELD OF INVENTION

This invention relates to novel antimitotic and anitisecretory peptides that are antagonists to the related peptides Bombesin and Gastrin Releasing Peptide which are useful in controlling; (1) the growth of small cell lung and prostatic carcinomas, and (2) gastric acid secretions, causative and symptomatic of peptic (esophageal, gastric, and duodenal) ulcers.

BACKGROUND OF INVENTION

Bombesin is a 14 amino acid peptide, originally isolated from the skin of the frog *Bombina bombina*. Bombesin is known to have a range of effects including induction of gastric and pancreatic secretion, stimulation of the nervous system, induction of myoelectric and contractile activity of intestinal myocytes, reduction of renal blood flow, secretion of pituitary hormones, and growth promotion.

Gastrin Releasing Peptide (GRP), a 27 amino acid peptide, was isolated later in mammals, and found to have an identical carboxy terminus to bombesin, with analogous properties. Further, gastrin releasing peptide and the structurally related bombesin have been shown to compete for binding to high affinity receptors on small cell lung carcinoma cells (SCLC), and prostatic endothelial cells. Binding with any of these growth factors causes measurable [$^3$H] thymidine uptake and clonal growth.

Many studies have implicated cell growth factors in tumor cell growth by activation of growth factor receptors. In this regard, Bombesin/GRP and receptor activation is related to other well-known growth factors and oncogenes. There has been considerable interest in the design and development of competitive bombesin receptor antagonist as possible antimitotic agents since the discovery that these peptides, bombesin and GRP, act as potent autocrine growth factors in human small cell lung and possibly also prostatic carcinoma systems. Underlying support for this approach comes from experiments utilizing anti-bombesin monoclonal antibodies to prevent binding of their receptor and eliciting a mitogenic response. Experiments using monoclonal antipeptide antibodies demonstrated clonal growth inhibition, of SCLC cells invitro and in xenografts of nude mice invivo. The mitogenic response begins with the production of intracellular signals by the ligand-receptor complex. For GRP/bombesin, this includes activation of a G-protein, which in turn activates phospholipase C (PLC). PLC converts phosphatidylinositol phosphate (PI) into inositol 1,4,5,-triphosphate (IP$_3$) and diacylglycerol (DAG). IP$_3$ and DAG are believed to be intracellular signals of the GRP/bombesin receptor pathway activation.

After Bombesin/GRP cell receptors were established on SCLC cells, receptors were also found to be present on human prostate cells. Subsequent studies also firmly established the growth effects of bombesin/GRP on prostatic epithelial cells in vitro utilizing bombesin/GRP antibodies. Further, cell proliferation studies of PC3 (a human prostatic carcinoma cell line) and PMU23 (a epithelial cell line from a primary culture of a stage III prostatic carcinoma) demonstrated a dose dependent Bombesin/GRP growth curve. This data suggest that there may be an autocrine or paracrine enhancement of tumor cell growth within the prostrate gland. Therefore, interrupting the effect of GRP/bombesin maybe useful for treating the progression of prostatic cancers where these factors are acting as autocrine or paracrine mitotic agents.

Bombesin and GRP are also capable of inducing gastric and pancreatic secretion and have demonstratable saturable receptors on cells of pancreatic (B-Cells) and intestinal (C-cells) origin, and therefore, antagonist of these receptors may serve in treatment of peptic ulcers and intestinal and pancreatic disorders, and may extend to adenocarinomas of these tissues.

Studies with the anti-bombesin/GRP antibodies lead to the hypothesis that it may be possible to disrupt the autocrine growth cycle of bombesin/GRP using designed peptide receptor antagonists. Since then several types of Bombesin antagonist have been reported. These antagonist have been defined by type and position of the substitutions of the natural sequence. Early receptor antagonist suffered from low potency, lack of specificity, and toxicity which presented serious problems with their scientific and therapeutic use.

More recent work has concentrated on modification of the carboxy terminal (C-terminal) region of these peptides to interrupt the receptor interaction utilizing a variety of different types of C-terminal modified analogs. These have included incorporation of D-amino acids, non-peptide bonds for example (ψ[CH$_2$NH]), amide, and ester modifications. These alterations gave rise to certain peptides having improved characteristics.

The applicants have prepared peptide derivatives having N-terminal alkanoyl groups of from 6 to 18 carbon atoms which have markedly improved antagonistic properties relative to the bombesin receptor. The peptide antagonists of this invention potentially possess significant antimitotic and/or antisecretory activity and therefore may allow for a scientifically interesting and therapeutically significant adjunct to cancer therapy and the treatment of ulcers.

SUMMARY OF THE INVENTION

Claimed are peptide derivatives of the formula

wherein
X is a straight, branched, or cyclic alkanoyl group of from 6 to 18 carbon atoms;
A$_1$ is Gln, His, his, MeHis, Mehis, His(τMe), his(τMe), His(πMe), his(πMe), Ala, Val, Leu, leu, MeLeu, Meleu, Ile, Pro, Phe, phe, Met, Trp, Lys, Arg, aNpa, Glu(OMe), glu(OMe), pGlu, pglu, Glu, or glu;
A$_2$ is Trp, MeTrp, Ser, Thr, Asn, Gln, Tyr, Met, Phe(Sub), Lys, Lys(pClCbz) or Cha,;
A$_3$ is Ala, MeAla, Aib, Phe, phe, Phe(Sub), phe(Sub), bNpa, Arg, Glu, Gln, Gly, Asn, Cys, Ser, Thr, Tyr, Val, Leu, Ile, Pro, Met, Trp, Nle, or Abu;
A$_4$ is Val, MeVal, Gln, Gly, Asn, Cys, Ser, Ala, Leu, Ile, Pro, Phe, Phe(pSub), Met, Trp, Nle, Abu, bNpa, Thr, or Thr(Bzl);

A₅ is Gly, Ser, ser, Ser(Bzl), ser(Bzl), Thr, Asn, Gln, Tyr, Trp, Phe, phe, Phe(Sub), phe(Sub), Sar, ala, pro, lys, Asp, arg, lys(pClCbz), Ac³c, Ac⁵c, or Ac⁶c;

A₆ is His, Ser, Thr, Asn, Gln, Tyr, Trp, His, Lys, Lys(Cbz), Arg, Tyr, Phe, phe, Phe(pSub), phe(pSub), His, MeHis, His(τMe), His(πMe), Aib, Nle, Nva, Ser, Ser(Bzl), Glu, Asp, Asp(OtBu), or bNpa;

A₇ is a bond or is Leu, leu, MeLeu, Meleu, Phe, Ala, Val, MeVal, Ile, MeIle, Pro, Met, Trp, Ser, Thr, Asn, Gln, Tyr, Trp, Nle, MeNle, Nva, MeNva, or Glu;

Y is a carboxy terminal residue selected from OH, (C₁–C₈) alkoxy ester, carboxamide, mono or di (C₁–C₄) alkyl amide, (C₁–C₄) alkylamine, (C₁–C₄) thioalkylether, or a pharmaceutically acceptable salt thereof and certain pharmaceutical uses thereof.

DETAILED DESCRIPTION OF THE INVENTION

The following common abbreviations of; (1) amino acids and their three letter codes, (2) modified and unusual amino acids, and (3) terminal amino and carboxy substituents used throughout this specification:

(1): THE AMINO ACIDS AND THEIR THREE LETTER CODE
L-AMINO ACIDS
Ala - alanine
Arg - arginine
Asn - asparagine
Cys - cysteine
Gly - glycine
Glu - glutamic
Val - valine
Gln - glutamine
His - histidine
Ile - isoleucine
Leu - leucine
Lys - lysine
Phe - phenylalanine
Met - methionine
Pro - proline
Ser - serine
Thr - threonine
Trp - tryptophan
Tyr - tyrosine
(2): MODIFIED AND UNUSUAL AMINO ACIDS
Ac3c - 1-amino-1-cyclopropanecarboxylic acid
Ac5c - 1-amino-1-cylcopentanecarboxylic acid
Ac6c - 1-amino-1-cylcohexanecarboxylic acid
Asp(OtBu) - O-t-butylaspartic acid
Abu - α-amino-n-butyric acid
Aib - 2-aminoisobutyric acid
Cha - cyclohexylalanine
Chg - cyclohexylglycine
His(πMe) - Nπ-methyl histidine
His(τMe) - Nτ-methyl histidine
Hyp - hydroxyproline
pGlu - pyroglutamic acid
glu(OMe) - gamma-methyl-D-glutamic acid
Tyr(I) - 3-idodotyrosine (Tyr(I)),
3,5-diiodotyrosine (Tyr(I₂)
Lys(Cbz) - benzyloxycarbonyl lysine
Lys(pClCbz) - p-chlorobenzyloxy lysine
MeLys - N-methyllysine
MeLeu - N-methylleucine
MeHis - N-methylhistidine
MeTrp - N-methyltryptophan
MeAla - N-methylalanine
MeVal - N-methylvaline
MeNle - N-methyl(2S)-2aminohexanoic acid
MeNva - N-methyl-(2S)-2-aminopentanoic acid
MeIle - N-methylisoleucine
MePhe - N-methylphenylalanine
MePgl - N-phenylglycine
aNpa - α-(naphthyl)alanine
bNpa - β-(naphthyl)alanine
Mnl - 3,4-dihydroproline
Nle - norleucine
Nva - norvaline
Orn - ornithine
Pip - pipecolate
Pba - p-aminophenylbutyric acid
Phe(pSub) - para substituted phenylalanine,
  Phe(pCl) - parachlorophenylalanine,
  Phe(pBr) - parabromophenylalanine,
  Phe(pFl) - parafluorophenylalanine,
  Phe(pNO₂) - paranitrophenylalanine
Pgl - phenylglycine
Ser(Bzl) - benzylserine
Sar - sarcosine (N-methylglycine)
Phe(Sub) - ortho, meta, or para, mono- or di-substituted phenylalanine
Tha - β-(2-thienyl)-alanine
Thr(Bzl) - benzylthreonine
Trp(Bzl) - benzyltryptophan
Tiq - Tetrahydroisoquinoline 3-carboxylate
AMINO AND CARBOXY TERMINAL ACID SUSTITUENTS
Ac - acetyl
Azt - azetidine-2-carboxylate
Cin - cinnamoyl
DhCin - 3,4-dihydrocinnamoyl
Glt - glutaryl
Mal - maleyl
Oac - 8-aminooctanoic acid
Oct - n-octy
Suc - succinyl
Glt - glutaryl
Tfa - trifloroacetyl
C-terminal amide
Amino Acids & Modifications The naturally occurring amino acids, with the exception of glycine, contain a chiral carbon atom. Unless otherwise specifically indicated, the optically active amino acids, referred to herein, are of the L-configuration. For example, any of the amino acids of the A₁ or A₇ group can be of the D- or L-configuration. According to convention the code for a particular amino acid beginning with a lower case letter indicates the amino acid is of the D-configuration, while a code beginning with an upper case letter can indicate either the L-configuration or both the D-and L-configurations as context indicates. As is customary, the structure of peptides written out herein is such that the amino terminal end is on the left side of the chain and the carboxy terminal end is on the right side of the chain.

An alkanoyl group of from 6 to 18 carbon atoms is taken to include straight, branched, cyclic, saturated and unsaturated acyl groups optionally having from 1 to 4 double bonds, for example, n-hexanoyl, isohexanoyl, cyclohexanoyl, cyclopentylcarbonyl, heptanoyl, and octanoyl, n-decanoyl, n-undecanoyl, n-dodecanoyl, n-tridecanoyl, n-tetradecanoyl, 3,7-dimethyloctanoyl, 2,4-dimethylhexadecanoyl, 1,7,10-trimethylundecanoyl, n-pentadecanoyl, n-hexadecanoyl, eicosoyl, n-heptadecanoyl, 3-propylnonanoyl, 10-undecanoyl, 15 3,7,11-trimethyl-2,6, 10-pentadecatrienoyl, 5,9-dimethyl-2,4,8-decatrienoyl, 4,6-dimethyloct-3-3noyl, 1,2,5,9- tetramethyl-2,4,8-decatrienoyl, 2-hexadecanoyl, lauroyl, myristicoyl, palmitoyl, aleicoyl, linoleicoyl, γ-linolenicoyl, and stearoyl.

The term "any amino acid" as used herein does not purport to include any carboxylic acid having an amino substituent, but rather is used as it is commonly used by those skilled in the art of polypeptide derivatives and includes the naturally occurring amino acids as well as other "non-protein" a-amino acids commonly utilized by those in the peptide chemistry arts when preparing synthetic analogs of naturally occurring peptides. The naturally occurring amino acids are glycine, alanine, valine, leucine,isoleucine, serine, methionine, threonine, phenylalanine, tyrosine, tryptophan, cysteine, proline, histidine, aspartic acid, asparagine, glutamic acid, glutamine, arginine, ornithine, and lysine. Also included would be the D-isomers of the naturally occurring amino acids; D-alanine, D-valine, D-leucine, D-isoleucine, D-serine, D-methionine, D-threonine, D-phenylalanine, D-tyro-sine, D-tryptophan, D-cysteine, D-proline, D-histidine, aspartic acid, D-asparagine, D-glutamic acid, D-glutamine, D-arginine. Also included are "non-protein" α-amino acids, examples are 1-amino-1-cyclopropanecarboxylic acid (Ac3c), 1-amino-1cylcopentanecarboxylic acid (Ac5c), 1-amino-1 cylcohexanecarboxylic acid(Ac6c), O-t-butylaspartic acid (Asp(OtBu), α-amino-n-butyric acid (Aba), (2S)-2-aminohexanoic acid (norleucine)(Nle), (2S)-2-aminopentanoic acid (norvaline)(Nva), Nπ-methylhistidine (His(πMe)), N$^\tau$-methylhistidine (His(τMe)), N-methyllysine (MeLys), N-methylleucine (MeLeu), N-methylhistidine (MeHis), N-methyltryptophan (MeTrp), N-methylalanine (MeAla), N-methylvaline (MeVal), N-methyl-(2S)-2aminohexanoic acid (MeNle), N-methyl-(2S)-2-aminopentanoic acid (MeNva), N-methylisoleucine (MeIle), N-methylphenylalanine (MePhe), N-methylphenylglycine (MePgl), β-(2-thienyl)alanine (Tha), benzylthreonine (Thr(Bzl)), benzyltryptophan (Trp (Bzl)) norleucine, norvaline, alloisoleucine, homoarginine, thiaproline, dihydroproline, hydroxyproline (Hyp), homoserine, cyclohexylglycine (Chg), α-amino-n-butyric acid (Aba), cyclohexylalanine (Cha), aminophenylbutyric acid (Pba), phenylalanines mono or disubstituted at the ortho, meta, or para, such as para substituted phenylalanine (Phe(pSub)) and para-chlorophenylalanine, para-aminophenylalanine and para-nitrophenylalanine or positions of the phenyl moiety with one or two of the following, a ($C_1$–$C_4$) alkyl, ($C_1$–$C_4$) alkoxy, halogen, or nitro groups or substituted with a methylenedioxy group, β-2- and 3-thienylal-alanine, β-2- and 3-furanylalanine, β-2-, 3-,and 4-pyridylalanine, β-(benzothienyl-2- and 3-yl)alanine, β-(1- and 2-naphthyl)alanine(Npa), O-alkylated derivates of serine, threonine, or tyrosine, methyl esters of glutamic and aspartic acid, S-alkylated cysteine, the O-sulfate ester of tyrosine, and halogenated tyrosines such as 3-idodotyrosine, and 3,5-diiodotyrosine.

Groups of α-amino acids can be defined by certain charge characteristics. There are two general characteristics of side chains: nonpolar and polar. The nonpolar residues are made up of the hydrophobic residues which includes those with aliphatic hydrocarbon side chains: Gly, Ala, Val, Leu, Ile, Nle, Pro and the aromatic group Phe and Trp, and the pseudohydrocarbon, Met. The polar amino acids are made up three groups: (1) The acidic hydrophobic residues, (2) the neutral residues, and (3) basic hydrophobic residues. The neutral residues contains the hydroxyl-containing residues, Ser and Thr; the amides, Asn and Gln; aromatic rings, Tyr and Trp; the sulfhydryl groups, Cys, and small structurally accommodating amino acids Ala and Gly. In the polar class are "Acidic hydrophilic" residues that include aspartic acid, glutamic acid, and tyrosine and the "basic hydrophilic" residues that include His, Lys, and Arg.

Y designates the chemical group(s) that may be utilized to substitute or modify the terminal amino acid. Therefore, Y may be a carboxamide, alkoxy ester, alkylamide, alkyl amine, or thioalkylether.

The polypeptides of formula 1 can form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower) alkylpiperidine, and any other suitable amine.

The ability of the peptide derivatives of this invention to act as antagonists of Bombesin/GRP can be demonstrated by the ability of such peptides to compete with radioiodinated bombesin/GRP for mammalian bombesin/GRP receptors using the method of Buck, et al., *Science* 226: 987–989, 1984, and by the ability of such compounds to stimulate or to inhibit bombesin/GRP induced phosphatidylinositol turnover using the method of Bristow, et al., *British J. Pharmacol.* 90: 211–21, 1987.

As with any generic group of chemical compounds, certain groups are preferred. Applicants prefer those peptide derivatives of formula 1 wherein:

X is a straight, branched, or cyclic alkanoyl group of from 6 to 18 carbon atoms;

$A_1$ is Gln, His, his, MeHis, Mehis, His(τMe), his(τMe), His(πMe), or his(πMe);

$A_2$ is Trp or MeTrp;

$A_3$ is Ala MeAla, Val, Leu, or Ile;

$A_4$ is Val, MeVal, Gly, Ala, Leu, Ile, or Nle;

$A_5$ is Gly or ala;

$A_6$ is His; MeHis, His(τMe), or His(πMe);

$A_7$ is a bond or is Leu, leu, MeLeu, Meleu, Ala, Val, MeVal, Ile, MeLie, Nle, MeNle, Nva, or MeNva; and Y is a carboxy terminal residue selected from OH, (C1–$C_8$) alkoxy ester, carboxamide, mono or di ($C_1$–$C_4$) alkylamide, ($C_1$–$C_4$) alkyl amine, ($C_1$–$C_4$) thioalkylether, or pharmaceutically acceptable salt thereof.

More preferred are peptide derivatives of formula 1 wherein

X is an alkanoyl group of from 6 - 10 carbon atoms;

$A_1$ is Gln or His;

$A_2$ is Trp;
$A_3$ is Ala;
$A_4$ is Val;
$A_5$ is Gly;
$A_6$ is His;
$A_7$ is a bond or is Leu; and
Y is a carboxy terminal residue selected from OH or amino.

Most preferred are those compounds of formula 1 wherein
X is a straight, branched, or cyclic alkanoyl group of from 7–9 carbon atoms, especially octanoyl;
$A_1$ is Gln or His;
$A_2$ is Trp;
$A_3$ is Ala;
$A_4$ is Val;
$A_5$ is Gly;
$A_6$ is His;
$A_7$ is a bond or is Leu; and
Y is a carboxy terminal residue selected from OH or amino.

Peptide Synthesis

The peptides of this invention can be prepared by a variety of procedures readily known to those skilled in the art. Such procedures include the solid phase sequential and block synthesis, gene cloning and combinations of these techniques. The solid phase sequential procedure can be performed using established automated methods such as by use of an automated peptide synthesizer. In this procedure, the peptides were synthesized on the resin beginning with a protected dipeptide containing a inter-amino acid thiomethlene methylene sulfoxide bridge with the C-terminal amino acid attached to a methylbenzhydrylamine resin. The extension of the peptide sequence was done using standard methodology and that of the manufacturer and that known by people skilled in the art.

After completion of coupling of the sequence either the Boc protecting group was left in place or it was removed and the N-terminal amino group acylated. Displacement of the protected fragment from the resin was accomplished using the hydrogen fluoride procedure.

The α-amino protecting group employed with each amino acid introduced into the polypeptide sequence may be any such protecting group known to the art. Among the classes of α-amino protecting groups contemplated are (1) acyl type protecting groups such as: formyl, trifluoroacetyl, phthalyl, toluenesulfonyl (tosyl), benzenesulfonyl, nitrophenylsulfenyl, tritylsulfenyl, o-nitrophenoxyacetyl and α-chlorobutyryl; (2) aromatic urethan type protecting groups such as benzyloxycarbonyl and substituted benzyloxycarbonyl, such as p-chlorobenzyloxycarbonyl, p-nitrobenzyl- carbonyl, p-bromobenzyloxycarbonyl, p-methoxybenzyloxycarbonyl, 1-(p-biphenylyl)-1-methylethoxycarbonyl, α, α-dimethyl-3,5-dimethoxybenzyloxycarbonyl and benzhydryloxycarbonyl; (3) aliphatic urethan protecting groups such as tert-butyloxycarbonyl (Boc), diisopropylmethoxycarbonyl, isopropyloxycarbonyl, ethoxycarbonyl and allyloxycarbonyl; (4) cycloalkyl urethane type protecting groups such as cyclopentyloxycarbonyl, adamantyloxycarbonyl and cyclohexyloxycarbonyl; (5) thiourethane type protecting groups such as phenylthiocarbonyl; (6) alkyl type protecting groups such as triphenylmethyl (trityl) and benzyl; and (7) trialkylsilane groups such as trimethylsilane. The preferred a-amino protecting group is tert-butyloxycarbonyl (Boc).

As is known in the art of solid phase peptide synthesis many of the amino acids bear functionalities requiring protection during the chain preparation. The use and selection of the appropriate protecting group is within the ability of those skilled in the art and will depend upon the amino acid to be protected and the presence of other protected amino acid residues on the peptide. The selection of such a side chain protecting group is critical in that it must be one which is not removed by cleavage during cleavage of the protecting group of the α-amino moiety. For example, suitable side chain protecting groups for lysine are benzyloxycarbonyl and substituted benzyloxycarbonyl, said substituent being selected from halo (e.g., chloro, bromo, fluoro) and nitro (e.g., 2-chlorobenzyloxycarbonyl, p-nitrobenzyloxy-carbonyl, 3,4-dichlorobenzyloxycarbonyl), tosyl, t-amyloxycarbonyl, t-butydiisopropyl and diisopropylmethoxycarbonyl. The alcoholic hydroxyl group of threonine and serine can be protected with an acetyl, benzoyl, tert-butyl, trityl, benzyl, 2,6-dichlorobenzyl or benzyloxycarbonyl group. The preferred protecting group is benzyl.

The selection of an appropriate coupling reagent is within the skill of the art. A particularly suitable coupling reagent where the amino acid to be added is Gln, Asn or Arg is N,N'-diisopropylcarbodiimide and 1-hydroxybenzotriazole. The use of these reagents prevents nitrile and lactam formation. Other coupling agents are (1) carbodiimides (e.g., N,N'-dicyclohexylcarbodiimide and N-ethyl-N'-(y-dimethylaminopropylcarbodiimide); (2) cyanamides (e.g., N,N-dibenzylcyanamide); (3) ketenimines; (4) isoxazolium salts (e.g., N-ethyl-5-phenyl-isoxazolium-3'-sulfonate; (5) monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyl-di-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., Boc-Ala-O-Ala-Boc), (8) nitrogen containing heterocyclic compounds having a hydroxy group on one ring nitrogen (e.g., N-hydroxyphthalimide, N-hydroxysuccinimide and 1-hydroxybenzotriazole), and (9) diphenyl phosphorylazide. Other activating reagents and their use in peptide coupling are described by Kapoor, *J. Pharm. Sci.,* 59, pp. 1–27 (1970). Applicants prefer the use of the symmetrical anhydride as a coupling reagent for all amino acids except Arg, Asn and Gln.

Each protected amino acid or amino acid sequence is introduced into the solid phase reactor in about a four-fold excess and the coupling is carried out in a medium of dimethylformamide: methylene chloride (1:1) or in dimethylformamide alone or preferably methylene chloride alone. In cases where incomplete coupling occurs, the coupling procedure is repeated before removal of the α-amino protecting group, prior to the coupling of the next amino acid in the solid phase reactor. The success of the coupling reaction at each stage of the synthesis is monitored by the ninhydrin reaction as described by E. Kaiser et al, *Analyt. Biochem.* 34, 595 (1970).

Following the coupling of the α-amino protected amino acid to the resin support, the protecting group is removed using any suitable procedure such as by using trifluoroacetic acid in methylene chloride, trifluoroacetic acid alone, or HCl in dioxane. The deprotection is carried out at a temperature of between 0° C. and room temperature. Other standard cleaving reagents and conditions for removal of specific α-amino protecting groups may be used. After removal of the α-amino protecting group the other amino protected amino acids are coupled step-wise in the desired order. Alternatively, multiple amino acid groups may be coupled by the solution method prior to coupling with the resin supported amino acid sequence.

After the desired amino acid sequence has been obtained, the peptide is removed from the resin. This can be done by hydrolysis such as by treatment of the resin bound polypeptide with an amino acid alcohol and acetic acid in dichloromethane (DCM) Protecting groups can be removed by procedures well known in the art. Typically protecting group removal is done after the peptide chain synthesis is complete but the protecting groups can be removed at any other appropriate time. Purification of peptides is principally accomplished through preparative reversed phase high performance liquid chromatography and those techniques known to those skilled in the art.

Therapeutic Use

The natural history of peptic ulcer disease is one of recurrent exacerbations and remissions. As a result, ulcerative diseases should be treated as a chronic disorder. Peptic (esophageal, gastric, and duodenal) ulcers occur in areas of the gastrointestinal tract exposed to acid and pepsin. The compounds of the present invention, which are useful in the treatment of gastrointestinal and/or pancreatic ulcers and may be effective in resultant hypersecretions occurring from the pancrease and/or stomach, particularly hydrochloric acid and pepsin. As such compounds of this invention may serve as an appropriate intervention to treat peptic ulcers.

The appropriate dose of a peptide derivative of this invention when used in the treatment of peptic ulcers is from 0.2 mg/kg to 250 mg/kg of patient body weight per day depending on factors such as the patient, the severity of the peptic ulcer to be treated and the peptide derivative selected. The suitable dose for a particular patient can be readily determined. Preferably from 1 to 4 daily doses would be administered typically with from 5 mg to 100 mg of active compound per dose. The amount of a peptide of this invention required to inhibit gastric acid secretion can be readily determined by those skilled in the art.

Use of bombesin/GRP analogs in cancer therapy is indicated for the treatment of SCLC and prostatic carcinomas and prevention of a variety of other cancer conditions. Those experienced in this field are readily aware of the circumstances requiring cancer therapy. The term "patient" used herein is taken to mean mammals such as primates, including humans, sheep, horses, cattle, pigs, dogs, cats, rats and mice.

As used herein, the term "tumor tissue" means both benign and malignant tumors or neoplasms and includes melanomas, lymphomas, leukemias, and sarcomas. Illustrative examples of tumor tissues are cutaneous such as malignant melanomas and mycosis fungoides; hematologic tumors such as leukemias, for example, acute lymphoblastic, acute myelocytic, or chronic myelocytic leukemia; lymphomas such as Hodgkin's disease or malignant lymphoma; gynecologic tumors such as ovarian and uterine tumors; urologic tumors such as those of the prostate, bladder, or testis; soft tissue sarcomas, osseus, or non-osseous sarcomas, breast tumors; tumors of the pituitary, thyroid, and adrenal cortex; gastrointestinal tumors such as those of the esophagus, stomach, intestine, and colon; pancreatic and hepatic tumors; laryngeae papillomestasas and lung tumors.

The term "controlling the growth" and the concept of treating a cancer means slowing, interrupting, arresting, or stopping the growth and metastases of a rapidly proliferating tumor in a warm blooded animal; it being understood that treatment in a warm blooded animal does not generally provide a "cure" for the tumor in the sense that necessarily the tumor tissue is destroyed or totally eliminated.

The appropriate dose of a peptide derivative of this invention when used in the treatment of, or controlling the growth of a cancer or tumor tissue, including small cell lung carcinomus or prostatic cancers is from 0.2 mg/kg to 250 mg/kg of patient body weight per day depending on factors such as the patient, the severity of the small cell lung carcinoma to be treated and the peptide derivatives selected. The suitable dose for a particular patient can be readily determined. Preferably from 1 to 4 daily doses would be administered typically with from 5 mg to 100 mg of active compound per dose. The amount of a peptide of this invention required to inhibit SCLC growth can be readily determined by those skilled in the art.

It is generally known that therapeutic agents used in the treatment of cancer can be used in conjunction with other therapeutic agents or therapies known to be useful in the treatment of cancer. The peptides of invention can also be used in conjunctive therapy. For example, a peptide of structure 1 can be administered in conjunction with surgical excision of the tumor or with radiation therapy, immunotherapy, or local heat therapy. In the preferred mode of treating cancer a peptide of structure 1 are administered in conjunction with a chemical cytotoxic agent known to be useful for tumor therapy. Illustrative chemical cytotoxic agents are cyclophosphamide, methotrexate, prednisone, 6-mercaptopurine, procarbazine, danorubicin, chlorambucil, cytosine arabinoside, 6-thioguanine, thio TEPA, 5-fluorouracil, 5-fluoro-2-deoxyuridine, 5-azacytidine, nitrogen mustard, 1,3-bis(2-chloroethyl)-1-nitrosourea (BCNU), 1-(2-chloroethyl)-3-cyclohexyl-1-nitrosourea (CCNU), busulfan, adriamycin, bleomycin, vindesine, cycloeucine, or methylglyoxal bis(guanylhydrazone) (MGBG). When such combination therapy is employed, the effect of the cytotoxic agent may be potentiated. The remission produced by the cytotoxic agent may be enhanced and regrowth of the tumor may be slowed or prevented. Use of such combination therapy therefore allows for smaller doses or fewer individual doses of the cytotoxic agent to be employed. The term "combination therapy" contemplates the administration of a peptide of structure 1 immediately prior to the beginning of therapy with a cytotoxic agent, concurrently with such therapy, or during the time immediately following the cessation of such therapy. When such combination therapy is employed for the treatment of a tumor the cytotoxic agent may be administered at a dosage known in the art to be effective for treating the tumor. However, a peptide of structure 1 may produce an additive or synergistic effect with a cyctotoxic agent against a particular tumor. Thus when such combination antitumor therapy is used, the dosage of the cytotoxic agent administered may be less than that administered when the cytotoxic agent is used alone. In combination with a peptide derivative of structure 1, the cytotoxic agent may, therefore, be administered at a lower dosage or at less frequent intervals as compared to the cytotoxic agent used alone. Similarly when combination therapy is used, the dosage or frequency of administration of a peptide of structure 1 may be less than when used without a cytotoxic agent.

Although some of the peptide derivatives may survive passage through the gut following oral administration, applicants prefer non-oral administration, for example, subcutaneous, intravenous, intramuscular or intraperitoneal;

administration by depot injection; by implant preparation; or by application to the mucous membranes, such as, that of the nose, throat and bronchial tubes, for example, in an aerosol can containing a peptide derivative of this invention in a spray or dry powder form.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

EXAMPLES

This invention is illustrated by the following, nonlimiting examples.

EXAMPLE 1

PREPARATION OF N-(n-Octanoyl)-Gln-Trp-Ala-Val-ala-His-Leu-NH$_2$

The peptide was synthesized on p-methylbenzhydrylamine resin using N$^\alpha$-t-Boc protected amino acids and octanoic acid that were coupled with the Bop reagent (ref. Dung Le-Nguyen, Annie Heitz and Bernard Castro, *J. Chem. Soc., Perkin Trans.* I (1987) 1915–1919. Upon completion of the synthesis, the peptide was deprotected and removed from the resin by treatment with liquid HF containing 10% anisole for 1 hour at 0° C. Upon removal of the HF in vacuo, the peptide was precipitated with Et$_2$O and filtered. The peptide was then extracted from the resin with 30% aqueous acetic acid and glacial acetic acid. The wash was lyophilized to give the crude peptide, which was purified by HPLC. The peptide was analyzed by amino acid analysis, fast-atom bombardment-mass spectroscopy and analytical HPLC.

In a similar manner the compounds of Examples 2–4 are prepared.

EXAMPLE 2

N-(Lauroyl)-Gln-Trp-Ala-Val-ala-His-Leu-NH$_2$

EXAMPLE 3

N-(Palmitoyl)-Gln-Trp-Ala-Val-ala-His-Leu-NH$_2$

EXAMPLE 4

N-(n-Octanoyl)-Gln-Trp-Ala-Val-ala-His-NH$_2$

The compounds of examples 1–4 have the following physical and chemical properties.

| Compound | Amino Acid Analysis | | | | | FAB-MS |
|---|---|---|---|---|---|---|
| (Example #) | Glx | Ala | Val | Leu | His | (M + H)$^+$ |
| 1 | 1.01 (1) | 2.01 (2) | 0.97 (1) | 1.02 (1) | 0.99 (1) | 949.5 |
| 2 | 1.03 (1) | 2.00 (2) | 0.96 (1) | 1.02 (1) | 0.98 (1) | 1005.5 |
| 3 | 1.04 (1) | 1.98 (2) | 0.98 (1) | 1.03 (1) | 0.98 (1) | 1061.5 |
| 4 | 1.09 (1) | 1.94 (2) | 0.88 (1) | — | 1.09 (1) | 836.4 |

EXAMPLE 5

AFFINITY FOR THE BOMBESIN RECEPTOR AS DEMONSTRATED BY COMPETITION AT THE RECEPTOR FOR IODINATED GRP

The pancreata from one or more mice were pooled, minced, and homogenized in 50 mM HEPES (pH 7.4) containing 120 mM NaCl and 5 mM KC1 at 4° C. and centrifuged at 37,500 xg for 15 minutes. The pellet was resuspended in 50 mM HEPES (pH 7.4) containing 10 mM EDTA and 300 mM KC1 and incubated for 30 minutes at 4° C. The suspension was centrifuged as above and the pellet was washed two times in 50 mM HEPES (pH 7.4) containing protease inhibitors (10 uM phenylmethylsulfonyl fluoride, 1 uM thiorphan, 40 ug/ml bacitracin, 10 mM iodoacetimide and 4 ug/ml leupeptin), and again centrifuged. The tissue was then resuspended in incubation buffer (1 ml per 4 mg pancreas) and incubated for 15 minutes at room temperature, then 250 ul was added to each assay tube to commence the assay. The assay tubes contained incubation buffer consisting of 50 mM HEPES (pH 7.4), 0.5% BSA, protease inhibitors, 2 mM MnCl$_{2, 1}$ uM somatostatin, and concentrations of $^{125}$I-GRP and peptides as needed in a final volume of 500 ul. The assay was allowed to proceed to equilibrium for 90 minutes at room temperature. After this time, the contents of each tube was rapidly filtered over Whatman GF/B filters presoaked in 0.1% polyethyleneimine and the filters were rapidly washed three times with ice-cold 50 mM HEPES (pH 7.4). Filter-bound radioactivity was quantitated in a gamma counter. Competition of iodinated GRP binding by test compounds or standards was expressed as a percentage of $^{125}$I-GRP binding in the absence of peptide. Affinity and maximal binding were calculated with Ligand (Biosoft, Cambridge, UK).

EXAMPLE 6

ANTAGONISM OF THE BOMBESIN RECEPTOR AS DEMONSTRATED BY THE EFFECT ON PHOSPHATIDYLINOSITOL TURNOVER

Pancreata from mice were pooled and chopped at 350 pm with a tissue chopper. The chopped tissue was washed twice with Krebs-Hepes, then incubated for 30 minutes in 37° C. Krebs-Hepes buffer with fresh buffer after 15 minutes. The tissue was then incubated in this buffer containing 100–200 $\mu$Ci of $^3$H-inositol at 37° C. for 1 hour. The tissue was then washed twice and incubated for another 30 minutes in Krebs-Hepes (containing 10 mM Li+) at 37° C. with fresh buffer change after 15 minutes. Portions of the tissue mass (approximately 10 mg per assay tube) were then placed in Li+ buffer with protease inhibitors, (40 ug/ml bacitrain, 4 ug/ml leupeptin, 4 ug/ml chymostatin, 20 ug/ml thiorphan), 0.1% BSA, and then 0.1–1000 nM peptide was added in 25 $\mu$l in a final volume of 250 $\mu$l. To measure antagonism portions of the tissue in Li+ buffer were pretreated with 1 uM of the potential antagonist for 5 minutes at 25° C. before the addition of agonist (GRP). After 60 minutes at room temperature, the phosphatidylinositol turnover was terminated by the addition of 940 μl chloroform:methanol (1:2), followed by 310 μl chloroform, followed by 310 μl water. Each tube was then vortexed for 5 seconds and then centrifuged at 2500 xg for 8 minutes to separate the phases. 900 μl of the top (aqueous) phase was then mixed with 2.1 ml water and loaded onto a 0.5 ml Biorad AG-1X8 (formate) ion exchange column. 50 μl of the bottom phase (chloroform) was withdrawn from each tube and placed in a counting vial, dried, and counted in scintillation fluid. The material on the columns was washed in order with: 1) 10 ml of water 2) 5 ml of 5 mM disodium tetraborate/60 mM sodium formate 3) 10 ml of 1 M ammonium formate in 0.1 M formic acid. The final (third) wash was collected and one ml was mixed with 10 ml of Bio-Safe scintillant and counted. The ratio of these counts (total inositol phosphates) to the corresponding organic phase counts was then calculated for each sample. The ratios in the presence of test compound and/or standards were then compared to the ratios for control tubes (i.e., no stimulating agonist). Dose-response lines were constructed and the abilities of test compounds to stimulate or to inhibit GRP induced phosphatidylinositol turnover were determined by graphical analysis or with the aid of a computer program.

Following the procedures of examples 5 and 6 with the compounds of examples 1–4, the following data was obtained.

| Compound (Example #) | Bombesin Receptor Binding[1] (Example 5) | Antagonism |
|---|---|---|
| 1 | ++ | + |
| 2 | + | + |
| 3 | + | + |
| 4 | ++ | + |

[1] + indicates $K_D$ < 500 nM   ++ indicates $K_D$ < 50 nM

TABLE OF PEPTIDES TESTED FOR:
(1) RECEPTOR BINDING AND (2) PI TURNOVER
Peptides were tested according to the protocols descrive for receptor binding and for PI turnover previously described.

| Sequence | Binding $K_D$(nM) | PI Turnover Agonist | Antagonist |
|---|---|---|---|
| pQ Q R L G N Q W A V G H L M # | 0.15 | + | ND |
| Nα-AcetylQ W A V a H L # | 69 | – | + |
| Nα-OctylQ W A V a H L # | 5.0 | – | + |
| Nα-LaurylQ W A V a H L # | 320 | – | + |
| Nα-PalmitylQ W A V a H L # | 350 | – | + |
| Nα-AcetylQ W A V a H # | 1500 | – | + |
| Nα-OctylQ W A V a H # | 58 | – | ± |
| Nα-LaurylQ W A V a H # | >10,000 | ND | ND |
| Nα-PalmitylQ W A V a H # | >10,000 | ND | ND |
| Nα-AcetylW A V a H # | >10,000 | ND | ND |
| Nα-OctylW A V a H # | >10,000 | ND | ND |
| Nα-LaurylW A V a H # | >10,000 | ND | ND |
| Nα-PalmitylW A V a H # | >10,000 | ND | ND |

What is claimed is:

1. A peptide derivative of the formula

wherein
X is a straight, branched, or cyclic alkanoyl group from 7–9 carbon atoms;
$A_1$ is Gln or His;
$A_2$ is Trp;
$A_3$ is Ala;
$A_4$ is Val;
$A_5$ is Gly;
$A_6$ is His;
$A_7$ is a bond or is Leu; and
Y is a carboxy terminal residue selected from OH or amino.

2. A peptide derivative of claim 1 wherein
X is octanoyl;
$A_1$ is Gln or His;
$A_2$ is Trp;
$A_3$ is Ala;
$A_4$ is Val;
$A_5$ is Gly;
$A_6$ is His;
$A_7$ is a bond or is Leu; and
Y is a carboxy terminal residue selected from OH or amino.

3. A peptide derivative of claim 1 which is

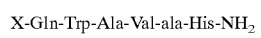

wherein X is octanoyl.

4. A peptide derivative of claim 1 which is

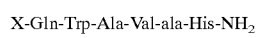

wherein X is lauroyl or palmitoyl.

5. A peptide derivative of claim 1 which is

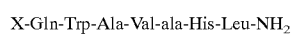

wherein X is octanoyl.

6. A peptide derivative of claim 1 which is

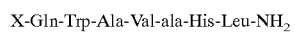

wherein X is lauroyl.

7. A peptide derivative of claim 1 which is

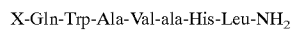

wherein X is palmitoyl.

8. A method of treating small cell lung carcinoma in a patient in need thereof which comprises administering to the patient an effective amount of a peptide derivative of claim 1.

* * * * *